United States Patent
Commons et al.

[11] Patent Number: 5,977,170
[45] Date of Patent: Nov. 2, 1999

[54] ELEVATION OF HDL CHOLESTEROL BY 4-[(AMINOTHIOXOMETHYL)HYDRAZONO]-4-ARYLBUTYL CARBAMATES

[75] Inventors: Thomas Joseph Commons, Wayne; Susan Christman, Philadelphia, both of Pa.

[73] Assignee: American Home Products Corporation, Madison, N.J.

[21] Appl. No.: 09/096,089

[22] Filed: Jun. 11, 1998

Related U.S. Application Data

[60] Provisional application No. 60/049,704, Jun. 16, 1997.
[51] Int. Cl.$^6$ ............... C07C 255/27; C07C 271/10; A61K 31/27
[52] U.S. Cl. .............. 514/481; 558/445; 560/24; 560/27; 560/28; 560/29; 560/30; 560/31; 560/33; 560/163; 560/115; 514/488; 514/489
[58] Field of Search ............... 558/445; 560/30, 560/24, 29; 549/491, 496, 505; 546/350; 514/481

[56] References Cited

U.S. PATENT DOCUMENTS 4,983,755  1/1991  Bühmann et al. .................. 560/24

FOREIGN PATENT DOCUMENTS 3624349  7/1986  Germany .

OTHER PUBLICATIONS

Russ et al., *Am. J. Med.*, 11:480–493 (1951).
Gofman et al., *Circulation*, 34:679–697 (1996).
Miller and Miller, *Lancet*, 1:16–19 (1975).
Gordon et al., *Circulation*, 79:8–15 (1989).
Stampfer et al., *N. England J. Med.*, 325:373–381 (1991).
Badimon et al., *Lab. Invest..*, 60:455–461 (1989).
Miller et al., *Br. Med. J.*, 282:1741–1744 (1981).
Picardo et al., *Arteriosclerosis.*, 6:434–441 (1986).
Glomset, *J. Lipid Res.*, 9:155–167 (1968).
Glass et al., *Circulation*, vol. 66, Suppl. II 102 (1982).
MacKinnon et al., *J. Biol. Chem.*, 261:2548–2552 (1986).
Grow and Fried, *J. Biol. Chem.*, 253:8034–8034–8041 (1978).
Lagocki and Scanu., *J. Biol. Chem.*, 255:3701–3706 (1978).
Schaefer et al., *J. Lipid Res..*, 23:1259–1273 (1982).
Tomita et al., *J. Heterocyclic Chem.*, 27:707–710 (1990).
Vega and Grundy, *Current Opinion in Lipidology*, 7:209–216 (1996).

*Primary Examiner*—Robert W. Ramsuer
*Assistant Examiner*—Ebenezer Sackey
*Attorney, Agent, or Firm*—Michael R. Nagy

[57] ABSTRACT

This invention relates to the treatment of atherosclerosis via raising the level of HDL cholesterol by administration of a compound of the formula

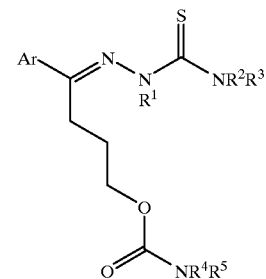

wherein
$R^1$, $R^2$, and $R^3$ are independently hydrogen, $C_1$–$C_6$ alkyl or —$(CH_2)_{0-6}$Ph where Ph is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R_4$ and $R_5$ are independently hydrogen, $C_1$–$C_6$ alkyl, $C_3$–$C_8$ cycloalkyl, or —$(CH_2)_{0-6}Ar^1$ where $Ar^1$ is phenyl, naphthyl, furanyl, pyridinyl or thenyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl, naphthyl, furanyl, pyridinyl or thienyl or Ar is optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH.

15 Claims, No Drawings

ELEVATION OF HDL CHOLESTEROL BY 4-[(AMINOTHIOXOMETHYL)HYDRAZONO]-4-ARYLBUTYL CARBAMATES

This application claims benefit of priority to provisional patent application Ser. No. 60/049,704 filed Jun. 16, 1997.

FIELD OF INVENTION

This invention relates to compounds useful in elevating high density lipoprotein, the "good" cholesterol. Compounds of this invention increase plasma levels of HDL in a cholesterol fed rat model and as such these compounds may be useful for treating diseases such as atherosclerosis.

BACKGROUND OF THE INVENTION

It is widely beleived that HDL is a "protective" lipoprotein [Gloria Lend Vega and Scott Grundy, Current Opinion in Lipidology, 7, 209–216 (1996)] and that increasing plasma levels of HDL may offer a direct protection against the development of atherosclerosis. Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.*, 11 (1951) 480–493; Gofman et al, *Circulation,* 34 (1966) 679–697; Miller and Miller, *Lancet,* 1 (1975) 16–19; Gordon et al., *Circulation,* 79 (1989) 8–15; Stampfer et al., *N. Engl. J. Med.,* 325 (1991) 373–381; Badimon et al., *Lab. Invest.,* 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated levels of some HDL particles in humans appears to be correlated to a descreased number of sites of stenosis in the coronary arteries of humans (Miller et al., *Br. Med. J.,* 282 (1981) 1741–1744).

There are several mechanisms by which HDL may protect against the progression of atherosclerosis. Studies in vitro have shown that HDL is capable of removing cholesterol from cells (Picardo et al., *Arteriosclerosis,* 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.,* 9 (1968) 155–167). This has been supported by experiments showing efficient transfer of cholesterol from HDL to the liver (Glass et al., *Circulation,* 66 (*Suppl. II*) (1982) 102; MacKinnon et al., *J. Biol. Chem.,* 261 (1986) 2548–2552). In addition, HDL may serve as a reservoir in the circulation for apoproteins necessary for the rapid metabolism of triglyceride-rich lipoproteins (Grow and Fried, *J. Biol. Chem.,* 253 (1978) 1834–1841; Lagocki and Scanu, *J. Biol. Chem.,* 255 (1980) 3701–3706; Schaefer et al., *J. Lipid Res.,* 23 (1982) 1259–1273). Accordingly, agents which increase HDL cholesterol concentrations are useful as anti-atherosclerotic agents, particularly in the treatment of dyslipoproteinemias and coronary heart disease.

BRIEF DESCRIPTION OF THE INVENTION

The compounds of this invention which elevate plasma levels of HDL cholesterol are represented by the formula

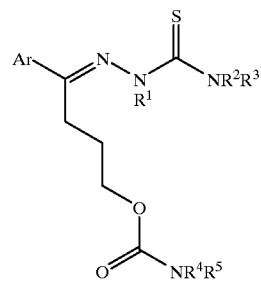

wherein
$R^1$, $R^2$, and $R^3$ are independently hydrogen, $C_1$–$C_6$ alkyl or —$(CH_2)_{0-6}$Ph where Ph is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R_4$ and $R_5$ are independently hydrogen, $C_1$–$C_6$ alkyl, $C_3$–$C_8$ cycloalkyl, or —$(CH_2)_{0-6}Ar^1$ where $Ar^1$ is phenyl, naphthyl, furanyl, pyridinyl or thenyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl, naphthyl, furanyl, pyridinyl or thienyl or Ar is optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH.

The compounds are tested in vivo in rats fed cholesterol-augmented rodent chow for 8 days according to the test protocol and blood from the rats analyzed for HDL cholesterol.

DETAILED DESCRIPTION OF THE INVENTION

The compounds of this invention are conveniently prepared by the routes shown in Scheme I and Scheme II. Specific examples are given in Experimental Section. These examples are for illustrative purposes only and are not to be construed as limiting to this disclosure in any way. Those skilled in the art will be aware of other methods of preparing compounds of this invention. The starting materials of intermediates are available commercially or can be prepared by standard literature procedures.

Scheme I

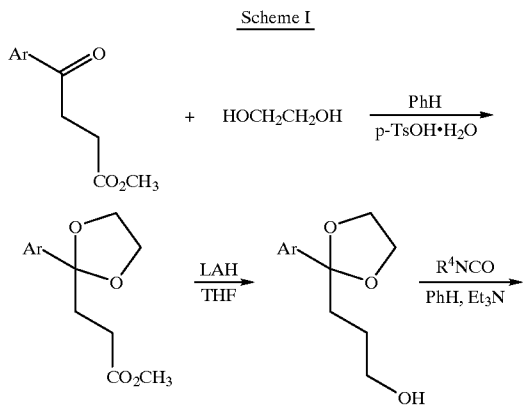

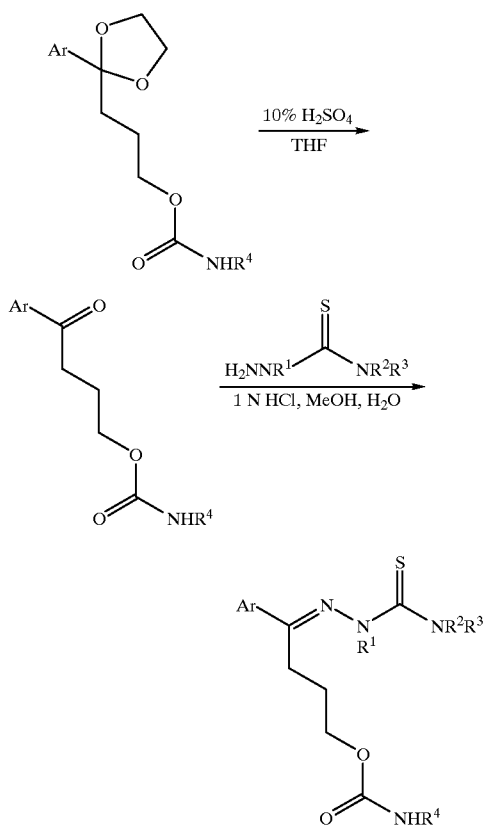

The synthetic route shown in Scheme II is preferred over the synthetic route presented in Scheme I in that the ketal prepared in the first step in Scheme I is obtained in low yield and is difficult to purify.

Scheme II

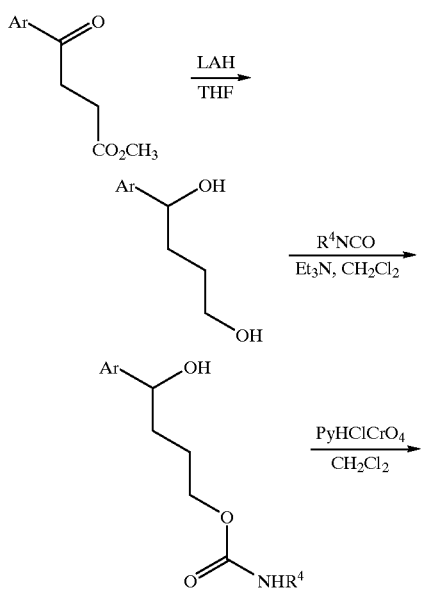

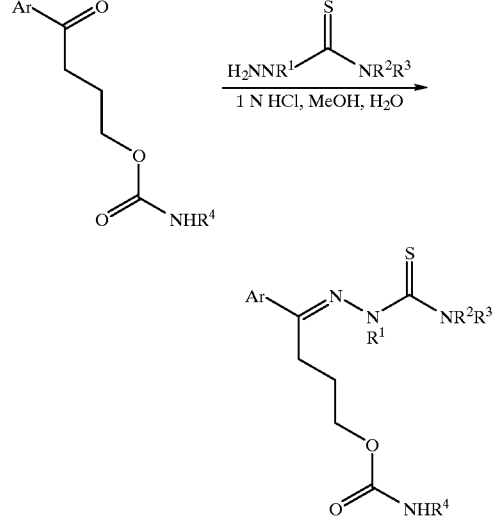

EXPERIMENTAL

Example 1
4-[(Aminothioxomethyl)hydrazono]-4-phenylbutylbutyl-carbamate (a) A mixture of methyl 3-benzoylpropionate (46.8 g, 0.24 mol), ethylene glycol (50 ml, 0.90 mol) and p-toluenesulfonic acid monohydrate (0.9096 g, 4.78 mmol) in 300 ml of benzene was refluxed under a nitrogen atmosphere and a Dean-Stark trap for 48 hours. The reaction was extracted five times with 5% NaHCO$_3$, dried (MgSO$_4$) and the solvent removed under reduced pressure to give 61.25 g of a yellow oil. Purification of this oil by chromatography on silica gel using ethyl acetate-hexane as the eluent gave methyl 3-benzoylpropionate ethylene ketal (14.7 g, 26%) as a yellow oil, FAB MS [M+H]$^+$ m/e=259.

Elemental Analysis for C$_{13}$H$_{16}$O$_4$

Calc'd: C, 66.09; H 6.83; N 0.00

Found: C, 65.87; H, 6.81; N, 0.23

(b) A solution of methyl 3-benzoylpropionate ethylene ketal (7.9661 g, 33.7 mmol), prepared in the previous step in 150 ml of anhydrous THF was added under nitrogen dropwise over 1 hour to a suspension of LAH (1.6656 g, 43.9 mmol) in 75 ml of anhydrous THF. After the addition the mixture was stirred at room temperature for 19 hours. Water (1.7 ml) was then added dropwise followed by the addition of 1.7 ml of 15% KOH and then 5.1 ml of water. The resulting mixture was stirred for 15 minutes and then filtered. The filtrate was concentrated under reduced pressure to remove most of the THF. The residue was partitioned between methylene chloride-water. The organic layer was separated and the aqueous layer extracted two times with methylene chloride. The combined organic extracts were dried (MgSO$_4$) and the solvent removed under reduced pressure to give 4-hydroxybutyrophenone ethylene ketal (6.51 g, 93%) as a white solid, mp 39–42° C.

Elemental Analysis for C$_{12}$H$_{16}$O$_3$

Calc'd: C, 69.21; H, 7.74; N, 0.00

Found: C, 69.44; H, 7.92; N, 0.10

(c) A solution of 4-hydroxybutyrophenone ethylene ketal (3.7595 g, 18.1 mmol), prepared in the previous step, butyl isocyanate (2.44 ml, 21.7 mmol) and triethylamine (2.52 ml, 18.1 mmol) in 100 ml of benzene was refluxed under nitrogen for 4 hours. By TLC the starting alcohol remained. An additional 1.00 ml (8.88 mmol) of butyl isocyanate was added and the reaction refluxed for 1.5 hours, stirred at room temperature overnight and then refluxed an additional 3 hours. The reaction was extracted two times with 1N HCl, fried (MgSO$_4$) and the solvent removed under reduced pressure to give the desired carbamic acid ketal as a clear oil. The material was used in the following step without additional purification, FAB MS [M+H]$^+$ m/e=308.

(d) A solution of the carbamic acid ketal (5.75 g, 18.7 mmol), prepared in the previous step, in 100 ml of THF plus 10 ml of 10% H$_2$SO$_4$ was stirred at room temperature for 32 hours. By TLC the reaction was not complete. An additional 100 ml of THF and 10 ml of 10% H$_2$SO$_4$ were added and the reaction stirred at room temperature for 24 hours. The reaction was concentrated under reduced pressure and the residue partitioned between methylene chloride and water. The organic layer was separated and the aqueous layer extracted two times with methylene chloride. The combined organic extracts were washed three times with water, fired (MgSO$_4$) and the solvent removed under reduced pressure to give 5.32 g of a white solid. By TLC some of the starting ketal remained. The residue was dissolved in 200 ml of THF plus 20 ml of 10% H$_2$SO$_4$ and the reaction stirred at room temperature for 3 days and then worked up as above to give 4.96 g of butyl-carbamic acid 4-oxo-4-phenyl-butyl ester as a white solid, mp 52–58° C.

Elemental Analysis for C$_{15}$H$_{21}$NO$_3$

Calc'd: C, 68.42; H, 8.04; N, 5.32

Found: C, 68.10; H 8.39; N, 6.19

(e) Thiosemicarbazide (1.5994 g, 17.5 mmol) was added to a solution of butyl-carbamic acid 4-oxo-4-phenyl-butyl ester (4.63 g, 17.6 mmol), prepared in the previous step, in 60 ml of methanol plus 4.7 ml of 1N HCl plus 4.7 ml of water and the reaction stirred at room temperature for 18 hours. The solid present was removed by filtration and the filtrate concentrated under reduced pressure during which time more solid formed. This solid was collected by filtration and combined with the first solid to give 4.2185 g of a white solid. Recrystallization of the solid from isopropyl alcohol gave the title compounds (3.0314 g, 51%) as a white solid, mp 120–123° C.

Elemental Analysis for C$_{16}$H$_{24}$N$_4$O$_2$S

Calc'd: C, 57.12; H, 7.19; N, 16.65

Found: C, 57.11; H, 7.13; N, 16.58

Examples 2 through 5 were prepared in the same manner as Example 1.

Example 2

4[(Aminothioxomethyl)hydrazono]-4-phenylbutylcylcohexylcarbamate

In Example 1, step (c) cyclohexyl isocyanate is substituted for butyl isocyanate. In step (e) the solid formed in the reaction mixture is collected by filtration. Recrystallization of this solid from isopropyl alcohol gave the title compound (3.1438 g, 57%) as a white solid, mp 136–140° C.

Elemental Analysis for C$_{18}$H$_{26}$N$_4$O$_2$S

Calc'd: C, 59.64; H, 7.23; N, 15.46

Found: C, 59.37; H, 7.23; N, 15.50

Example 3

2-[1-Phenyl-4-[[(phenylamino)carbonyl]oxy]butylidene]hydrazinecarbothioamide

In Example 1, step (c) phenyl isocyanate is substituted for isocyanate. In Step (e) the solid formed in the reaction mixture is collected by filtration and dried to give the title compound (3.7924 g, 86%) as a white solid, mp 140–142° C.

Elemental Analysis for C$_{18}$H$_{20}$N$_4$O$_2$S

Calc'd: C, 60.65; H, 5.66; N, 15.72

Found: C, 60.47; H, 5.84; N, 15.73

Example 4

Benzyl carbamic acid-4-[(aminothioxomethyl)hydrazono]-4-phenylbutyl ester

In Example 1, step (c) benzyl isocyanate is substituted for butyl isocyanate. In step (e) the solid formed in the reaction mixture is collected by filtration. Recrystallization of this solid from isopropyl alcohol gave the title compound (3.6380 g, 72%) as a white solid, mp 137–140° C.

Elemental Analysis for C$_{19}$H$_{22}$N$_4$O$_2$S

Calc'd: C, 61.60; H, 5.99; N, 15.12

Found: C, 61.30; H, 5.92; N, 15.17

Example 5

4-[(Aminothioxomethyl)hydrazono]-4-phenylbutyl(1-methylethyl)carbamate

In Example 1, step (c) isopropyl isocyanate is substituted for butyl isocyanate. In step (e) the solid formed in the reaction was collected by filtration and then dissolved in ethyl acetate and extracted five times with water. The organic phase was dried (MgSO$_4$) and the solvent removed under reduced pressure to give 2.73 g of a yellow solid. Recrystallization of this solid from isopropyl alcohol gave the title compound (2.19 g, 46%) as a light yellow solid, mp 122–125° C.

Elemental Analysis for C$_{15}$H$_{22}$N$_4$O$_2$S·0.3 C$_3$H$_8$O

Calc'd: C, 56.09; H, 7.22; N, 16.46

Found: C, 54.59; H, 7.19; N, 16.15

Example 6

N-Methyl-2-[1-phenyl-4-[[(phenylamino)carbonyl]oxy]butylidene]-hydrazinecarbothioamide a) Methyl 3-benzoylpropionate (50 g, 0.25 mol) in 300 ml of anhydrous THF was added under nitrogen dropwise over one hour to a suspension of LAH in 500 ml of anhydrous THF. After the addition the mixture was refluxed for 20 hours. After cooling to room temperature 14.3 ml of water was added dropwise followed by the addition of 14.3 ml of 15% KOH and then 42.9 ml of water. The mixture was stirred for 30 minutes and then filtered. The filtrate was concentrated under reduced pressure to remove the THF. The residue was partitioned between methylene chloride and 1 N HCl. The organic layer was separated and the aqueous layer extracted three times with methylene chloride. The organic extracts were combined, dried (MgSO$_4$) and the solvent removed under reduced pressure to give 4-phenyl-4-hydroxybutanol (37.90 g, 91%) as a white solid, mp 63–68° C.

Elemental Analysis for C$_{10}$H$_{14}$O$_2$

Calc'd: C, 72.26; H, 8.49; N, 0.00

Found: C, 72.19; H, 8.47; N, 0.05 b) A solution of 4-phenyl-4-4-hydroxybutanol (12.00 g, mmol), prepared in the previous step, phenyl isocyanate (7.8 ml, 71.8 mmol) and triethylamine (10.1 ml 72.5 mmol) in 500 ml of methylene chloride was stirred under nitrogen at room temperature for 23 hours. The reaction was extracted with 1 N HCl, dried (MgSO$_4$) and the solvent removed under reduced pressure to give 21.61 g of a clear oil. Purification of this oil on 1 kg of silica gel (230–400 mesh) using 5%–10% ethyl acetate-methylene chloride as the eluent gave phenyl-carbamic acid 4-hydroxy-4-phenyl-butyl ester (14.13 g, 65%) as a clear oil, MS m/e [M]$^+$ 285.

Elemental Analysis for C$_{17}$H$_{19}$NO$_3$·0.06 CH$_2$Cl$_2$·0.14 C$_4$H$_8$O$_2$ Calc'd: C, 70.06; H, 6.75; N, 4.64

Found: C, 69.00; H, 6.71; N, 4.53 c) Pyridinium chlorochromate (15.28 g, 70.9 mmol) was added to a solution of phenyl-carbamic acid 4-hydroxy-4-phenyl-butyl ester (13.48 g, 4.73 mmol), prepared in the previous step, in 300 ml of methylene chloride and the mixture stirred at room temperature for 2.5 hours. The reaction was poured onto 700 g of a silica gel (230–400 mesh) column made with methylene chloride. Eluting with 0.5%–1.5% ethyl acetate-methylene chloride gave phenyl-carbamic acid 4-oxo-4-phenyl-butyl ester (10.98 g, 82%) as a white solid, mp 121–123° C.

Elemental Analysis for $C_{17}H_{17}NO_3$

Calc'd: C, 72.07; H, 6.05; N, 4.94

Found: C, 72.16; H, 6.14; N, 4.90 d) Phenyl-carbamic acid 4-oxo-4-phenyl-butyl ester (2.80 g, 9.88 mmol), prepared in the previous step, was suspended in 60 ml of methanol and the mixture warmed to dissolve the solid. While still warm 2.7 ml of 1 N HCl, 2.7 ml of water and 4-methyl-3-thiosemicarbazide (1.04 g, 9.92 mmol) were added and the reaction stirred under nitrogen for 21 hours. The solid formed was removed by filtration and dried under high vacuum to give the title compound (3.07 g, 84%) as a white solid, mp 155–157° C.

Elemental Analysis for $C_{19}H_{22}N_4O_2S$

Calc'd: C, 61.60; H, 5.99; N, 15.12

Found: C, 61.84; H, 5.99; N, 15.25

Example 7

4-[(Aminothioxomethyl)hydrazono]-4-phenylbutyl 1-naphthalenylcarbamate

1-Naphthyl isocyanate (4.3 ml, 30 mmol) in 50 ml of methylene chloride was added under nitrogen dropwise over 1 hour to a solution of 4-phenyl-4-hydroxybutanol (5.00 g, 30 mmol), prepared in step (a) of Example 6, and triethylamine (4.2 ml, 30 mmol) in 200 ml of methylene chloride at room temperature. After the addition the reaction was stirred at room temperature for 18 hours. The solid present in the reaction was removed by filtration. The filtrate was extracted with 1 N HCl, dried (MgSO$_4$) and the solvent removed under reduced pressure to give 10.08 g of a clear oil. Purification of the oil by chromatography on 1 kg of silica gel (230–400 mesh) using 3%–20% ethyl acetate-methylene chloride as the eluent gave naphthalen-1-yl-carbamic acid 4-hydroxy-4-phenyl-butyl ester (7.73 g, 77%) as a white solid, mp 92–92° C.

Elemental Analysis for $C_{21}H_{21}NO_3$

Calc'd: C, 75.20; H, 6.31; N, 4.18

Found: C, 75.27; H, 6.40; N, 4.16

In the same manner as described in step (c) of Example 6, naphthalen-1-yl carbamic acid 4-oxo-4-phenyl-butyl ester (5.08 g, 86%) was isolated as a tan solid, mp 95–97° C.

Elemental Analysis for $C_{21}H_{19}NO_3 \cdot 0.08\ CH_2Cl_2$

Calc'd: C, 74.43; H, 5.68; N, 4.12

Found: C, 74.45; H, 5.77; N, 4.10

A suspension of naphthalen-1-carbamic acid 4-oxo-4-phenyl-butyl ester (4.72 g, 14 mmol), prepared in the previous step, in 100 ml of methanol plus 3.8 ml of 1 N HCl and 3.8 ml of water was warmed to dissolve the solid. While still warm thiosemicarbazide (1.29 g, 14 mmol) was added and the reaction stirred for 21 hours. The solid present was collected by filtration and dried under high vacuum to give the title compound (5.29 g, 92%) as a tan solid, mp 189–192° C.

Elemental Analysis for $C_{22}H_{22}N_4O_2S$

Calc'd: C, 65.00; H, 5.46; N, 13.78

Found: C, 65.10; H, 5.67; N, 13.69

Example 8

2-[1-Phenyl-4-[[(2-biphenylamino)carbonyl]oxy]butylidene]hydrazinecarbothioamide In the same manner as described in step 1 of Example 7, and replacing 1-naphthyl isocyanate with 2-biphenylyl isocyanate, biphenyl-2-yl-carbamic acid 4-hydroxy-4-phenyl-butyl ester (8.24 g, 73%) was isolated as a clear oil, MS m/e [M+H]$^+$ 362.

Elemental Analysis for $C_{23}H_{23}NO_3 \cdot 0.06\ CH_2Cl_2 \cdot 0.08\ C_4H_8O_2$ Calc'd: C, 75.17; H, 6.41; N, 3.75

Found: C, 74.39; H, 6.38; N, 3.63

In the manner as described in step(c) of Example 6, biphenyl-2-yl-carbamic acid 4-oxo-4-phenyl-butyl ester (6.91 g, 89%) was isolated as a white solid, mp 87–89° C.

Elemental Analysis for $C_{23}H_{21}NO_3$

Calc'd: C, 76.86; H, 5.89; N, 3.90

Found: C, 76.50; H, 5.95; N, 3.81

Biphenyl-2-yl-carbamic acid 4-oxo-4-phenyl-butyl ester (64.8 g, 18 mmol), prepared in the previous step, was suspended in 150 ml of methanol and the mixture warmed to dissolve the solid. While still warm 4.9 ml of 1 HCl, 4.9 ml of water and thiosemicarbazide (1.65 g, 18 mmol) were added and the reaction stirred under nitrogen for 23 hours. The reaction was concentrated under reduced pressure to remove the methanol. The residue was partitioned between methylene chloride and water. The organic layer was separated, extracted multiple times with water, dried (MgSO$_4$) and the solvent removed under reduced pressure to give 7.55 g of a white solid foam. Purification of this foam by chromatography on 1 kg of silica gel (200–300 mesh) using 5% ethyl acetate-methylene chloride as the eluent gave 6.65 g of a yellow solid. Recrystallization of this solid from isopropyl alcohol produced the title compound (4.88 g, 63%) as a white solid, mp 144–146° C.

Elemental Analysis for $C_{24}H_{24}N_4OS$

Calc'd: C, 66.64; H, 5.59; N, 12.95

Found: C, 66.72; H, 5.55; N, 13.08

Example 9

2-[1-(4-Methylphenyl)-4-[[(phenylamino)carbonyl]oxy]butylidene]-hydrazinecarbothioamide In the same manner as described in step (a) of Example 6, and replacing methyl 3-benzoylpropionate with 4-(4-methylphenyl)-4-oxobutyric acid, 1-p-tolyl-butane-1,4-diol was produced as an off-white solid, mp 43–47° C.

Elemental Analysis for $C_{11}H_{16}O_2$

Calc'd: C, 73.30; H, 8.95; N, 0.00

Found: C, 72.92; H, 8.80; N, 0.07

In the same manner as describe in step 1 of Example 7, and replacing 1-naphthyl isocyanate with phenyl isocyanate, phenyl-carbamic acid 4-hydroxy-4-4-p-tolyl-butyl ester (14.6 g, 81%) was isolated as a white solid, mp 69–72° C.

Elemental Analysis for $C_{18}H_{21}NO_3$

Calc'd: C, 72.22; H, 7.07; N, 4.68

Found: C, 72.02; H, 7.19; N, 4.49

In the same maenner as described in step (c) of Example 6, phenyl-carbamic acid 4-oxo-4-p-tolyl-butyl ester (13.3 g, 95%) was isolated as a white solid, mp 106–109° C.

Elemental Analysis for $C_{18}H_{19}NO_3$

Calc'd: C, 72.71; H, 6.44; N, 4.71

Found: C, 72.86; H, 6.13; N, 4.69

Phenyl-carbamic acid 4-oxo-4-p-tolyl-butyl ester (10.58 g, 36 mmol), prepared in the previous step, was suspended in 220 ml of methanol and the mixture warmed to dissolve the solid. While still warm 9.6 ml of 1 N HCl, 9.6 ml of water amd thiosemicarbazide (3.24 g, 36 mmol) were added and the reaction stirred under nitrogen for 22 hours. The solid formed was removed by filtration and recrystallized from methanol to give the title compound (10.5 g, 80%) as a white solid, mp 170–173° C.

Elemental Analysis for $C_{19}H_{22}N_4O_2S$

Calc'd: C, 61.60; H, 5.99; N, 15.12

Found: C, 61.72; H, 5.88; N, 15.09

Example 10
2-[4-[[[(3,4-Dichlorophenyl)amino]carbonyl]oxy]butylidene]-1-phenyl]-hydrazinecarbothioamide In the same manner as desceibed in step 1 of Example 7, and replacing 1-naphthyl isocyanate with 3,4-dichlorophenyl isocyanate, (3,4-dichloro-phenyl)-carbamic acid 4-hydroxy-4-phenyl-butyl ester (7.65 g, 71%) was isolated as a white solid, mp 86–89° C.

Elemental Analysis for $C_{17}H_{17}Cl_2NO_3$

Calc'd: C, 57.64; H, 4.84; N, 3.95

Found: C, 57.44; H, 4.81; N, 3.96

In the same manner as described in step (c) of Example 6, (3,4-dichloro-phenyl)-carbamic acid 4-oxo-4-phenyl-butyl ester (4.47 g, 95%) was isolated as a white solid, mp 141–143° C.

Elemental Analysis for $C_{17}H_{15}Cl_2NO_3$

Calc'd: C, 57.97; H, 4.29; N, 3.98

Found: C, 57.96; H, 4.26; N, 3.90

(3,4-Dichloro-phenyl)-carbamic acid 4-oxo-4-phenyl-butyl ester (4.32 g, 12.3 mmol) prepared in the previous step, was suspended in 200 ml of methanol and the mixture warmed to dissolve the solid. While still warm 3.3 ml of 1 N HCl, 3.3 ml of water and thiosemicarbazide (1.69 g, 18.5 mmol) were added and the reaction stirred under nitrogen for 19 hours. The solid was collected by filtration and recrystallized from isopropyl alcohol to give the title compound (2.69 g, 51%) as a white solid, mp 195–198° C.

Elemental Analysis for $C_{18}H_{18}C_{12}N_4O_2S$

Calc'd: C, 50.83; H, 4.27; N, 13.17

Found: C, 51.12; H, 4.23; N, 13.10

PHARMACOLOGY

In Vivo Assay: Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Procedure No. 352, modified for use with ninety-six well microtiter plates. After reconstitution with water the reagent contains 300 U/I cholesterol oxidase, 100 U/I horse radish peroxidase, 0.3 mmoles/14-aminoantipyrine and 30.0 mmoles/1 p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbance at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., J. Lipid Res., 32 (1991) 859–866. 25 µl of serum is injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45° C. The eluent is monitored by measuring absorbance at 490 nm and gives a continuous absorbance signal proportional to the cholesterol concentration. The relative concentration of each lipoprotein class is calculated as the per cent of total absorbance. HDL cholesterol concentration, in serum, is calculated as the per cent of total cholesterol as determined by FPLC multiplied by the total serum cholesterol concentration.

TABLE I

| Cholesterol Fed Rat | |
| --- | --- |
| Example | % Increase in HDL (Dose) |
| Example 1 | 134.0% (100 mg/kg) |
| Example 2 | 129.9% (100 mg/kg) |
| Example 3 | 150.0% (100 mg/kg) |
| Example 4 | 56% (100 mg/kg) |
| Example 5 | 97.9% (100 mg/kg) |
| Example 6 | 31.0% (100 mg/kg) |
| Example 7 | 33.4% (100 mg/kg) |
| Example 8 | 49.2% (100 mg/kg) |
| Example 9 | 26.7% (100 mg/kg) |
| Example 10 | 55.0% (100 mg/kg) |

PHARMACEUTICAL COMPOSITION

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties In suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to realease the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from high density lipoprotein insufficiency must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral or parenteral administration will be determined by the administering physician based on experience with the individual subject treated and standard medical principles.

Preferably the pharmaceutical composition is in unit dosage form, e.g., as tablets or capsules. In such form, the composition is sub-divided in unit doses containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A compound of the formula

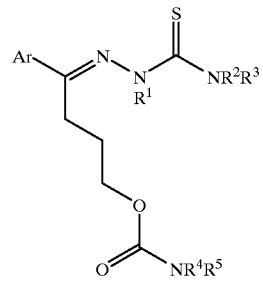

wherein:

$R^1$, $R^2$, and $R^3$ are independently hydrogen, $C_1$–$C_6$ alkyl or —$(CH_2)_{0–6}$Ph where Ph is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ $R^5$ are independently hydrogen, $C_1$–$C_6$ alkyl, $C_3$–$C_8$ cycloalkyl, or —$(CH_2)_{0–6}Ar^1$ where $Ar^1$ is phenyl or naphthyl, and $Ar^1$ may be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl or naphthyl, optionally substituted by halogen, cyano, nitro, $C_1$–$C_6$ alkyl, $C_1$–$C_6$ alkoxy, phenoxy, trifluoromethyl, $C_1$–$C_6$ alkoxycarbonyl, —$CO_2H$ or OH.

2. A compound according to claim 1 which is 4-[(aminothioxomethyl)hydrazono]-4-phenylbutyl butylcarbamate.

3. A compound according to claim 1 which is 4[(aminothioxomethyl)hydrazono]-4-phenylbutyl cyclohexylcarbamate.

4. A compound according to claim 1 which is 2-[1-phenyl-4-[[(phenylamino)carbonyl]-oxy]butylidene]hydrazinecarbothioamide.

5. A compound according to claim 1 which is benzyl carbamic acid-4-[(aminothioxomethyl)hydrazono]-4-phenyl-butyl ester.

6. A compound according to claim 1 which is 4-[(aminothioxomethyl)hydrazono]-4-phenylbutyl (1-methylethyl)carbamate.

7. A compound according to claim 1 which is N-methyl-2-[1-phenyl-4-[[(phenylamino)carbonyl]oxy]butylidene]-hydrazinecarbothioamide.

8. A compound according to claim 1 which is 4-[(aminothioxomethyl)hydrazono]-4-phenylbutyl 1-naphthalenylcarbamate.

9. A compound according to claim 1 which is 2-[1-phenyl-4-[[(2-biphenylamino)carbonyl]oxy]butylidene]hydrazinecarbothioamide.

10. A compound according to claim 1 which is 2-[1-(4-methylphenyl)-4-[[(phenylamino)carbonyl]oxy]butylidene] hydrazine-carbothioamide.

11. A compound according to claim 1 which is 2-[4-[[[(3, 4-dichlorophenyl)amino]carbonyl]oxy]butylidene]-1-phenyl]-hydrazinecarbothioamide.

12. A method of treating atherosclerosis in mammals which comprises administration to a mammal having atherosclerosis a therapeutically effective amount of a compound of the formula

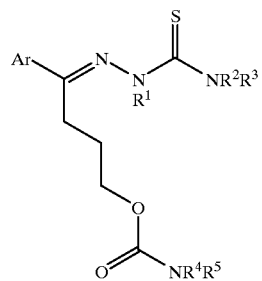

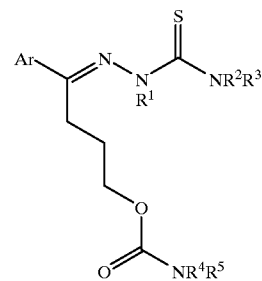

wherein:

R¹, R², and R³ are independently hydrogen, $C_1$–$C_6$ alkyl or —$(CH_2)_{0-6}$Ph where Ph is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

R⁴ R⁵ are independently hydrogen, $C_1$–$C_6$ alkyl, $C_3$–$C_8$ cycloalkyl, or —$(CH_2)_{0-6}Ar^1$ where $Ar^1$ is phenyl or naphthyl, and $Ar^1$ may be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl or naphthyl, optionally substituted by halogen, cyano, nitro, $C_1$–$C_6$ alkyl, $C_1$–$C_6$ alkoxy, phenoxy, trifluoromethyl, $C_1$–$C_6$ alkoxycarbonyl, —$CO_2H$ or OH.

13. The method according to claim 12 wherein the therapeutically effective compound is selected from the group consisting of:

4-[(aminothioxomethyl)hydrazono]-4-phenylbutyl butylcarbamate,

4[(aminothioxomethyl)hydrazono]-4-phenylbutyl cyclohexylcarbamate,

2-[1-phenyl-4-[[(phenylamino)carbonyl]-oxy]butylidene]hydrazinecarbothioamide, benzyl carbamic acid-4-[(aminothioxomethyl)hydrazono]-4-phenyl-butyl ester, 4-[(aminothioxomethyl)hydrazono]-4-phenylbutyl (1-methylethyl)carbamate, N-methyl-2-[1-phenyl-4-[[(phenylamino)carbonyl]oxy]butylidene]-hydrazinecarbothioamide, 4-[(aminothioxomethyl)hydrazono]-4-phenylbutyl 1-naphthalenylcarbamate, 2-[1-phenyl-4-[[(2-biphenylamino)carbonyl]oxy]butylidene]hydrazinecarbothioamide, 2-[1-(4-methylphenyl)-4-[[(phenylamino)carbonyl]oxy]butylidene]hydrazinecarbothioamide, and 2-[4-[[[(3,4-dichlorophenyl)amino]carbonyl]oxy]butylidene]-1-phenyl]-hydrazinecarbothioamide.

14. A pharmaceutical composition comprising a pharmaceutically acceptable carrier and a therapeutically effective amount of a compound of the formula wherein:

R¹, R², and R³ are independently hydrogen, $C_1$–$C_6$ alkyl or —$(CH_2)_{0-6}$Ph where Ph is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

R⁴ R⁵ are independently hydrogen, $C_1$–$C_6$ alkyl, $C_3$–$C_8$ cycloalkyl, or —$(CH_2)_{0-6}Ar^1$ where $Ar^1$ is phenyl or naphthyl, and $Ar^1$ may be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl or naphthyl, optionally substituted by halogen, cyano, nitro, $C_1$–$C_6$ alkyl, $C_1$–$C_6$ alkoxy, phenoxy, trifluoromethyl, $C_1$–$C_6$ alkoxycarbonyl, —$CO_2H$ or OH.

15. A composition according to claim 14 wherein the therapeutically effective compound is selected from the group consisting of:

4-[(aminothioxomethyl)hydrazono]-4-phenylbutylbutylcarbamate,

4[(aminothioxomethyl)hydrazono]-4-phenylbutyl cyclohexylcarbamate,

2-[1-phenyl-4-[[(phenylamino)carbonyl]-oxy]butylidene]hydrazinecarbothioamide, benzyl carbamic acid-4-[(aminothioxomethyl)hydrazono]-4-phenyl-butyl ester, 4-[(aminothioxomethyl)hydrazono]-4-phenylbutyl (1-methylethyl)carbamate, N-methyl-2-[1-phenyl-4-[[(phenylamino)carbonyl]oxy]butylidene]-hydrazinecarbothioamide, 4-[(aminothioxomethyl)hydrazono]-4-phenylbutyl 1-naphthalenylcarbamate, 2-[1-phenyl-4-[[(2-biphenylamino)carbonyl]oxy]butylidene]hydrazinecarbothioamide, 2-[1-(4-methylphenyl)-4-[[(phenylamino)carbonyl]oxy]butylidene]hydrazinecarbothioamide, and 2-[4-[[[(3,4-dichlorophenyl)amino]carbonyl]oxy]butylidene]-1-phenyl]-hydrazinecarbothioamide.

* * * * *